US006743231B1

(12) United States Patent
Gray et al.

(10) Patent No.: US 6,743,231 B1
(45) Date of Patent: Jun. 1, 2004

(54) TEMPORARY SPINAL FIXATION APPARATUSES AND METHODS

(75) Inventors: Eric L. Gray, Rockford, MN (US); Paul F. Boschert, St. Paul, MN (US)

(73) Assignee: Sulzer Spine-Tech Inc., Minneapolis, MN (US)

( * ) Notice: Subject to any disclaimer, the term of this patent is extended or adjusted under 35 U.S.C. 154(b) by 291 days.

(21) Appl. No.: 09/676,622

(22) Filed: Oct. 2, 2000

(51) Int. Cl.$^7$ .............................................. A61B 17/70
(52) U.S. Cl. ...................................................... 606/61
(58) Field of Search ............................. 606/61, 86, 99, 606/104, 60; 128/898

(56) References Cited

U.S. PATENT DOCUMENTS

| | | |
|---|---|---|
| 3,426,364 A | 2/1969 | Lumb |
| 4,369,769 A | 1/1983 | Edwards |
| 4,545,374 A | 10/1985 | Jacobson |
| 4,554,914 A | 11/1985 | Kapp et al. |
| 4,569,338 A | 2/1986 | Edwards |
| 4,653,481 A | 3/1987 | Howland et al. |
| 4,805,602 A | 2/1989 | Puno et al. |
| 5,000,165 A | 3/1991 | Watanabe |
| 5,127,912 A | 7/1992 | Ray et al. |
| 5,176,680 A | 1/1993 | Vignaud et al. |
| 5,190,543 A | 3/1993 | Schläpfer |
| 5,217,497 A | 6/1993 | Mehdian |
| 5,261,913 A | 11/1993 | Marnay |
| 5,300,073 A | 4/1994 | Ray et al. |
| 5,306,275 A | 4/1994 | Bryan |
| 5,312,404 A | 5/1994 | Asher et al. |
| 5,474,558 A | 12/1995 | Neubardt |
| 5,545,165 A | 8/1996 | Biedermann et al. |
| 5,549,608 A | 8/1996 | Errico et al. |
| 5,554,157 A | 9/1996 | Errico et al. |
| 5,571,109 A | 11/1996 | Bertagnoli |
| 5,586,984 A | 12/1996 | Errico et al. |
| 5,628,740 A | 5/1997 | Mullane |
| 5,720,751 A * | 2/1998 | Jackson ........................ 606/61 |
| 5,814,046 A | 9/1998 | Hopf |
| 5,863,293 A | 1/1999 | Richelsoph |
| 5,873,878 A * | 2/1999 | Harms et al. ................... 606/61 |
| 5,928,233 A * | 7/1999 | Apfelbaum et al. ........... 606/61 |
| 5,935,133 A | 8/1999 | Wagner et al. |
| 5,947,969 A * | 9/1999 | Errico et al. ................... 606/61 |
| 5,964,760 A | 10/1999 | Richelsoph |
| 6,010,503 A | 1/2000 | Richelsoph et al. |
| 6,050,997 A | 4/2000 | Mullane |
| 6,123,707 A | 9/2000 | Wagner |
| 6,139,549 A * | 10/2000 | Keller ........................... 606/61 |
| 6,162,234 A | 12/2000 | Freedland et al. |
| 6,179,841 B1 * | 1/2001 | Jackson ........................ 606/61 |
| 6,245,112 B1 | 6/2001 | Doubler et al. |
| 6,251,112 B1 * | 6/2001 | Jackson ........................ 606/61 |
| 6,299,648 B1 | 10/2001 | Doubler et al. |
| 6,355,068 B1 | 3/2002 | Doubler et al. |
| 6,375,657 B1 | 4/2002 | Doubler et al. |
| 6,440,171 B1 | 8/2002 | Doubler et al. |
| 6,551,323 B2 | 4/2003 | Doubler et al. |
| 2002/0143341 A1 | 10/2002 | Biedermann et al. |
| 2003/0023243 A1 | 1/2003 | Biedermann et al. |
| 2003/0073996 A1 | 4/2003 | Doubler et al. |
| 2003/0073997 A1 | 4/2003 | Doubler et al. |
| 2003/0074078 A1 | 4/2003 | Doubler et al. |
| 2003/0100904 A1 | 5/2003 | Biedermann |
| 2003/0149487 A1 | 8/2003 | Doulber et al. |

FOREIGN PATENT DOCUMENTS

| | | |
|---|---|---|
| DE | 4789-D E | 7/1990 |
| WO | WO 98/32386 | 7/1998 |

OTHER PUBLICATIONS

Brantigan, J. et al., "Posterior Lumbar Interbody Fusion Technique Using the Variable Screw Placement Spinal Fixation System", *SPINE: State of the Art Reviews*, vol. 6, No. 1, pp. 175–200 (Jan., 1992).
"Surgical Technique Step 11–Step 13",*Liberty Spinal System*, as described by Roger P. Jackson, M.D., F.A.C.S., pp. 18–20.
"Surgical Technique Step 5", *CD Horizon™ Spinal System*, as described by Samuel J. Laufer, M.D. et al., pp. 7–22.
Marchesi, D. et al., "Application of the AO–ASIF Universal Spine System in the Lumbosacral Junction", *Lumbosacral and Spinopelvic Fixation*, Eds. Margulies, J. et al., Chapter 24, pp. 293–299 (1996).
"PLIF (Posterior Lumbar Interbody Fusion) Broach System", *AcroMed® Corporation*, developed by Arthur D. Steffee, M.D.
"Posterior System Surgical Protocol", *Osteonics Spinal System*, pp. 12–17.
"Design Rationale", *TSRH® Spinal System*, p. 9.
"Products List—TSRH Instruments", *TSRH® Spinal Implant System*.
"Severe Spondylolisthesis of L5–S1 Grade 3 & 4", *TSRH®Pedicle Screw Spinal System*, Surgical Technique Step 9 as described by Edward H. Simmons, MD et al., p. 22–23.
"Contouring and Positioning the Rod" *Moss® Miami 3–Dimensional Spinal Instrumentation*, Product Catalogue, p. 8.
"Rod Reduction", *SDRS™*, Surgical Technique.
"The Universal Spinal System—Surgical Technique Guide for the Correction of Scoliosis", *Synthes® Spine*, pp. 5–13.
"The Universal Spinal System (USS) Technique Guide For Spondylolisthesis using the Side–Opening Screw and the Variable Axis Screw", *Synthes® Spine*, pp. 18–19.
"Hook Designs and Sizes", *XIA™ Spinal System*, pp. 4–5.

* cited by examiner

*Primary Examiner*—Todd E. Manahan
(74) *Attorney, Agent, or Firm*—Merchant & Gould P.C.

(57) ABSTRACT

Temporary spinal fixation apparatuses and methods are disclosed for temporarily fixing the relative position of spinal implant assemblies until a permanent fixation position is determined. The disclosed apparatuses and methods enhance the ease of placement of spinal implant assemblies and facilitates the accuracy of positioning of the spinal vertebrae. The invention can reduce the number of steps needed to perform spinal surgery and can decrease the likelihood of post-operative complications.

14 Claims, 9 Drawing Sheets

TEMPORARY SPINAL FIXATION APPARATUSES AND METHODS

FIELD OF THE INVENTION

This invention pertains to vertebral stabilization. Specifically, the invention is directed to vertebral implants and rod systems for stabilization of vertebral bodies and includes apparatuses and methods for temporary fixation until final alignment is established for permanent fixation.

BACKGROUND OF THE INVENTION

Chronic back problems cause pain and disability for a large segment of the population. In many cases, the chronic back problems are caused by intervertebral disc disease and loss of stability of the intervertebral joint. Stabilization and/or arthrodesis of the intervertebral joint can reduce the pain and debilitating affects associated with disc disease.

Spinal stabilization systems and procedures have been developed to stabilize diseased intervertebral joints and, in some cases, to fuse the vertebrae that are adjacent to the diseased joint space. One type of spinal stabilization system includes bone implants and rods that are used for many types of spinal conditions including, for example, degenerative disc disease, scoliosis, spondylolithisis, spinal stenosis, etc. Examples of some spinal stabilization systems are disclosed in U.S. Pat. Nos. 6,010,503; 5,946,760; 5,863,293; 5,554,157; 5,549,608; and 5,190,543, the entire disclosures of which are incorporated herein by reference. In these systems, a bone implant (e.g., pedicle screw, bone hook) is typically anchored to each vertebral body to be stabilized and a connecting rod mounted to each implant to fix the vertebrae in a particular position.

In many known stabilizing systems, after the implant is positioned in or on the bone, a connecting rod is mounted and secured to the implant by, for example, a locking nut that fixes the rod in position as the nut is tightened. Often times adjustment of the position of the vertebrae (e.g., compression, distraction, rotation, etc.), the implant or the rod necessitates repeated loosening and retightening of the locking nut until a satisfactory position is achieved. However, repeated loosening and tightening of the locking nut not only adds additional steps to the surgical procedure, and thus can increase the duration of the surgery, but the long term integrity of the implant, rod or implant assembly can potentially be compromised due to repeated threading and unthreading of the nut before arriving at a satisfactory final position.

Accordingly, there is a continuing need for instrumentation and procedures that enhance the ease of performing positional corrections, reduce surgical time and preserve the integrity of the implanted system to reduce the likelihood of post-operative complications. The present invention is directed to addressing these needs.

SUMMARY OF THE INVENTION

The invention is directed to temporary spinal fixation apparatuses and methods for temporarily fixing the relative position of vertebral bodies or spinal implants until a permanent fixation position is determined. The disclosed apparatuses and methods can enhance the ease of placement of spinal implant assemblies, facilitate the accuracy of positioning of spinal vertebrae and preserve the integrity of the fixation system.

It will be noted that in several places throughout the specification, guidance is provided through lists of examples. In each instance, the recited list serves only as a representative group. It is not meant, however, that the list is exclusive.

In one embodiment, a surgical instrument of the invention includes a temporary fixation device having a proximal end, a distal end and a fixing member passed within the lumen of an inner cannula that is passed within the lumen of an outer cannula. According to this embodiment, the fixing member can be axially mobile within the lumen of the inner cannula and the inner cannula axially mobile within the lumen of the outer cannula. The distal end of the instrument provides for mounting to a portion of the spinal implant assembly and the proximal end can be used for operating the device.

In another embodiment, a surgical instrument according to the invention can include an anti-torque device to reduce the amount torque applied to spinal vertebrae while performing a spinal implant procedure.

In another embodiment, a surgical instrument of the invention can be contained in a kit including temporary fixation devices having various inner and outer cannula lengths, various sized spinal implants, or other instruments used to perform a surgical procedure according to the invention.

The invention also provides methods for stabilizing the spinal column utilizing the instruments and principles disclosed herein.

DETAILED DESCRIPTION OF THE INVENTION

Figure 1:
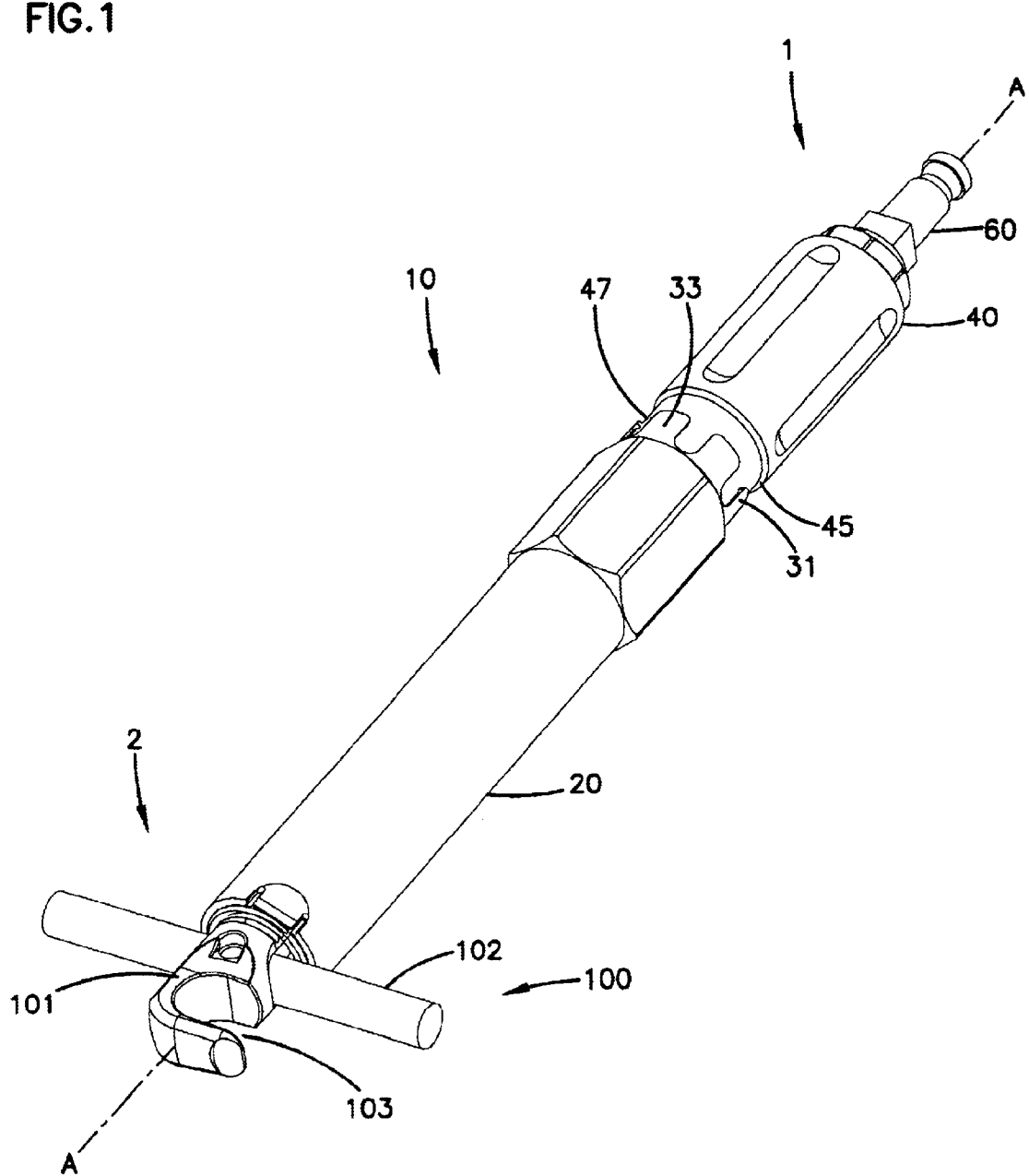
FIG. 1 is a perspective view of one embodiment of a temporary fixation device according to the invention.

The present invention is directed to instruments and methods for increasing the ease and accuracy of positioning vertebral bodies for stabilization and maintaining the integrity of spinal implant systems. The invention can reduce the number of steps and time required for placement of a vertebral stabilization system and thus reduce the overall surgery time. The invention is suited for use with known spinal implant assemblies including pedicle screws, laminar/transverse process hooks (collectively "hooks"), securing mechanisms, etc. and rods. The invention also provides unique advantages for pedicle screw systems having heads that provide multiple degrees of rotational or angular freedom.

In one embodiment, the invention provides a surgical instrument, particularly, a temporary fixation device ("TFD"), for temporarily fixing a stabilizing rod to a spinal implant prior to permanent fixation of the rod to the implant. A TFD provides enhanced control during positioning of the implant before or after temporary fixation. Moreover, the temporary fixation provided by a herein disclosed TFD permits the surgeon to repeatedly fix and unfix the rod to the implant when maneuvering or correcting the relative position of vertebrae without using the permanent securing arrangement of the implant until a permanent fixation position is established. This ensures the integrity of the permanent securing arrangement of the implant by requiring its use only when a final position is established and not using the permanent securing arrangement during corrective maneuvers that may be made prior to arriving at a final position. The ease and convenience provided by the instruments and methods of the invention permit the surgeon to align vertebrae into optimal position with greater ease and accuracy and in less time and with less chance of post-operative complications due to prolonged surgical time or compromise the integrity of the implant assembly.

As used herein, a "spinal implant assembly" refers to the combination of a spinal implant that can be attached, mounted, clasped, coupled, threaded or otherwise "anchored" to a vertebral body (e.g., posterior or anterior body, transverse process, etc.) and a stabilizing rod. At least one spinal implant is usually anchored to each vertebra to be stabilized. The stabilizing rod ("rod") can be positioned between two or more spinal implants and provides rigid stabilization between the vertebrae. Typically, two implants are positioned on each vertebrae, one on each side of the transverse process, to provide bilateral stabilization. Examples of spinal implants and rods suitable for the invention are known and disclosed in, for example, U.S. Pat. Nos. 6,010,503; 5,964,760; 5,863,293; 5,554,157; and 5,549,608, the entire disclosures of each of which are incorporated herein by reference.

As used herein, the term "permanent fixation" refers to the fixation of the vertebrae or implant in a final position with a securing arrangement that secures the rod to the implant at the completion of the surgical procedure and closure of the surgical site. In contrast, "temporary fixation" refers to fixation of the vertebrae or implant during surgery in a position that may or may not be the final position at the completion of the surgical procedure. In contrast to a permanent securing arrangement, a TFD of the invention is generally only used during surgery and is not left in the patient post-operatively. Prior to the invention, temporary fixation was typically provided during surgery by the permanent securing arrangement that secures the rod to the implant at the completion of the procedure.

Throughout the specification, unless stated otherwise, the terms "proximal" and "distal" are relative terms, the term "proximal" referring to a location nearest the surgeon and the term "distal" referring to a location farthest from the surgeon. Thus, for example, when describing an instrument, the proximal end is the end that is typically nearest the surgeon and the distal end nearest the patient.

DETAILED DESCRIPTION OF THE ILLUSTRATED EMBODIMENT

The invention will now be described with reference to the accompanying drawings, wherein like reference numerals identify identical or similar components throughout the several views. The illustrated embodiments and following description are for exemplary purposes to facilitate comprehension of the invention and should not be construed to limit the scope of the invention.

FIG. 1 is a perspective view of one embodiment of a temporary fixation device ("TFD") 10 shown mounted to one embodiment of a spinal implant assembly 100 suitable for the invention. Spinal implant assembly 100 includes spinal implant 101 and stabilizing rod 102. As illustrated, TFD 10 has a proximal end 1, a distal end 2 and a longitudinal axis A—A passing therethrough.

Figure 2:
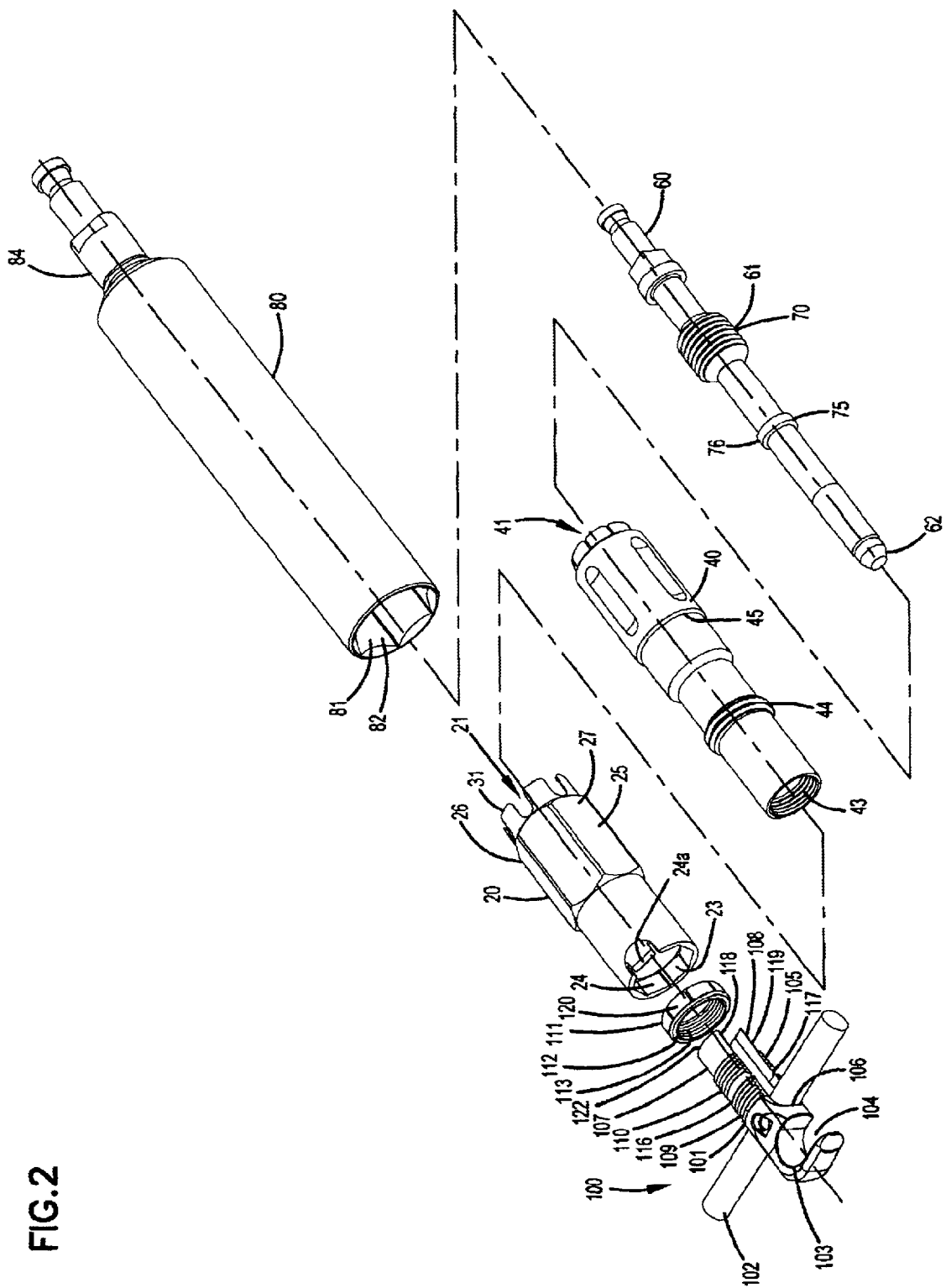
FIG. 2 is an exploded perspective view of a low profile version of the temporary fixation device of FIG. 1.

A shortened version of the TFD 10 of FIG. 1 is illustrated in an exploded perspective view in FIG. 2 and includes an outer cannula 20, inner cannula 40, fixing member 60 and driver 80. As illustrated, fixing member 60 is sized and configured to pass within lumen 41 of inner cannula 40. Inner cannula 40 is sized and configured to pass within lumen 21 of outer cannula 20. Driver 80 is sized and configured to pass over outer cannula 20.

Figure 3:
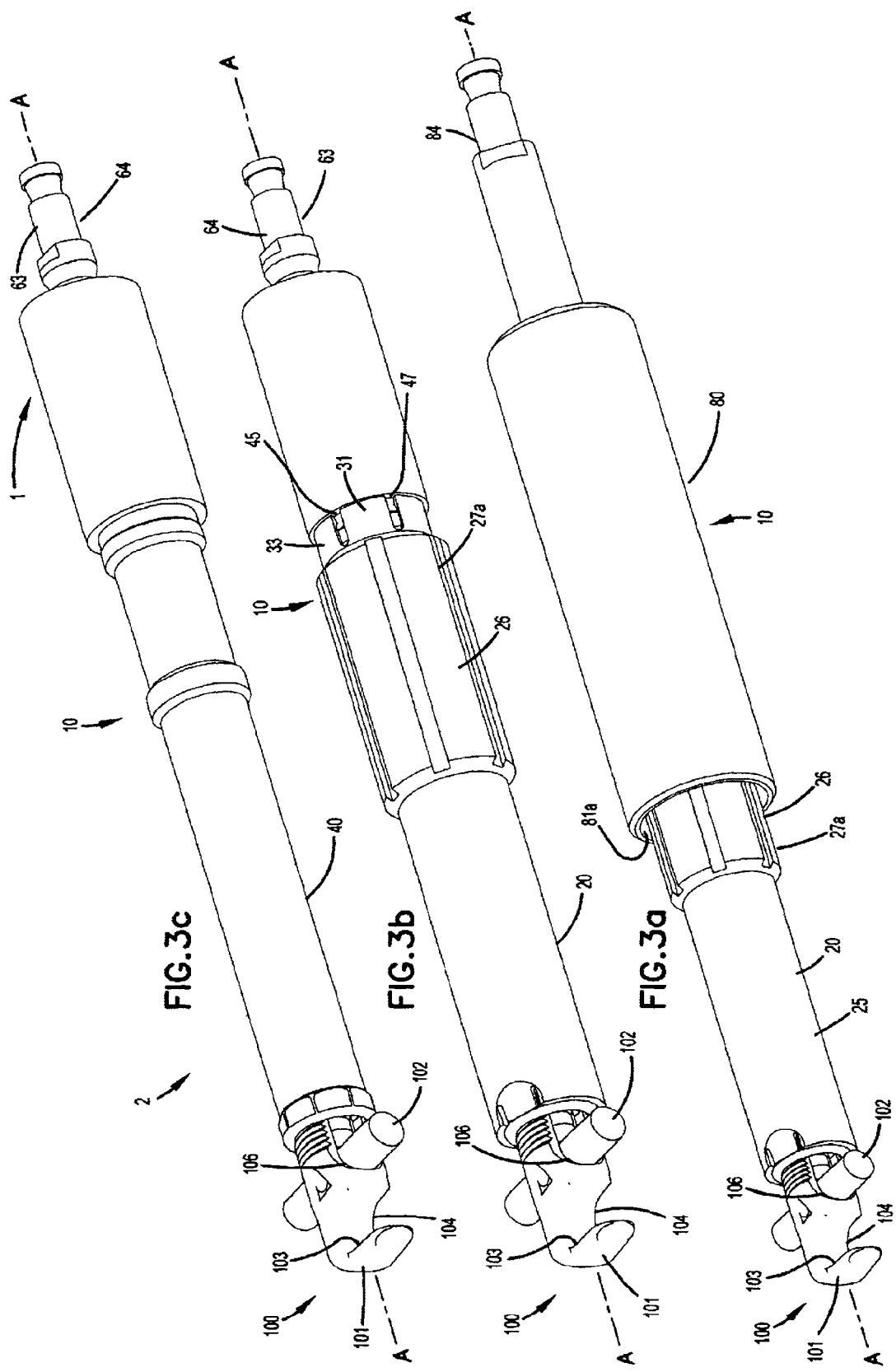
FIG. 3a is a perspective view of an alternative embodiment of a temporary fixation device of the invention.
FIG. 3b is the same embodiment of a temporary fixation device of FIG. 3b with the driver removed.
FIG. 3c is the same embodiment of a temporary fixation device of FIG. 3a with the outer cannula and driver removed.
Figure 4:
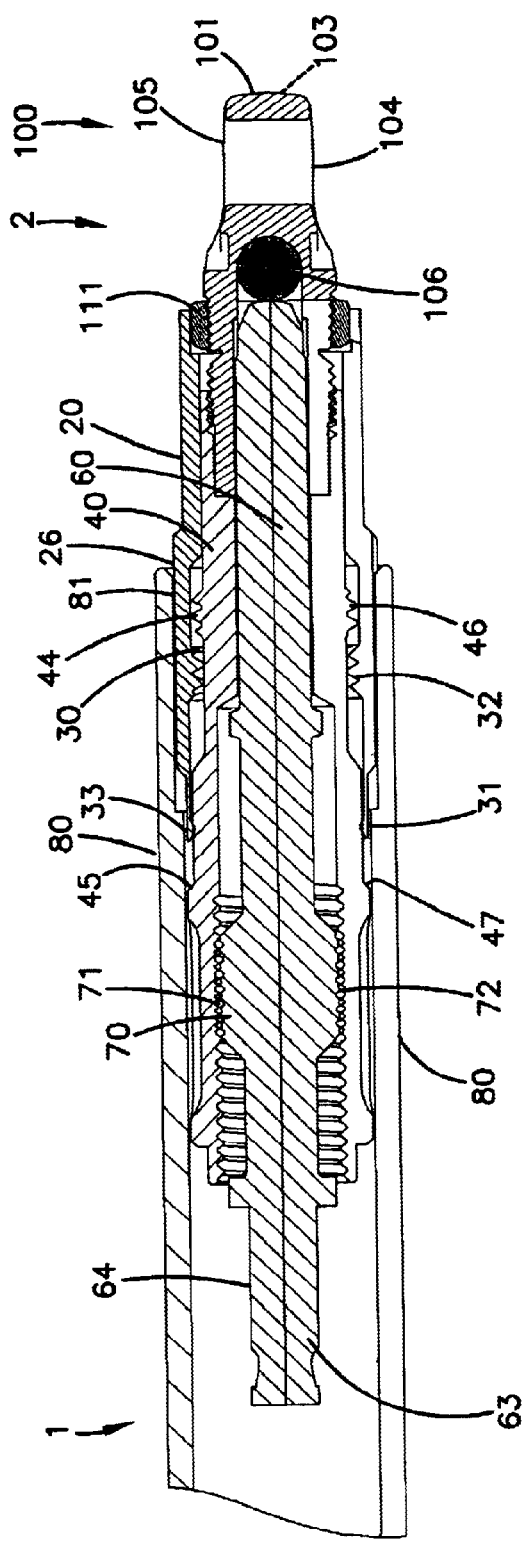
FIG. 4 is a longitudinal cross section of the temporary fixation device of FIGS. 3a–3c.

FIG. 3a is a perspective view of one embodiment of TFD 10 substantially identical to the embodiments of FIGS. 1 and 2 except that the driver engagement region 26 of outer cannula 20 has a splined configuration 27a to coaptate with cannula engagement region 81a of driver 80 as will be further described below. FIG. 3b illustrates the TFD 10 of FIG. 3a with driver 80 removed. FIG. 3c illustrates the TFD 10 of FIGS. 3a and 3b with outer cannula 20 removed. FIG. 4 is a longitudinal cross section view of the TFD 10 of FIG. 3a.

The operation and working relationship of the components of TFD 10 will be discussed with reference to spinal implant assembly 100. It will be appreciated that while the discussion exemplifies use of TFD 10 with spinal implant assembly 100, TFD 10 can be used with other spinal implant systems. For this discussion, the distal end of spinal implant 101 includes a hook 103 including a saddle region 104 for anchoring to a vertebral lamina or transverse process. Referring to FIG. 2, rod 102 is positioned within rod receiving arrangement 105 comprising cradle region 106 and arms 107 and 108. Arms 107 and 108 include a distal thread set 109 and a proximal thread set 110. It will be appreciated that spinal implant 101 includes a longitudinal axis that is concentric with longitudinal axis A—A of TFD 10 when TFD 10 is mounted to spinal implant 101 (see FIGS. 1 and 3a).

In use, when spinal implant assembly 100 is positioned on a spinal vertebrae, rod 102 can be securely fixed within cradle region 106 when locking nut 111 is threaded along distal threads 109 such that locking nut surface 112 is snugged tight against rod 102. In this particular spinal implant 101, the threads 113 of locking nut 111 are configured to force arms 107 and 108 together against rod 102 as locking nut 111 is distally advanced along distal threads 109 to a permanent tightened position. Grooves 116, 117 are present in each of arms 107, 108, respectively, between proximal threads 110 and distal threads 109. Grooves 116 and 117 provide a point at which tabs 118 and 119 of arms 107 and 108, respectively, can be removed from implant 101 after permanently fixing rod 102 with locking nut 111.

Figure 5:
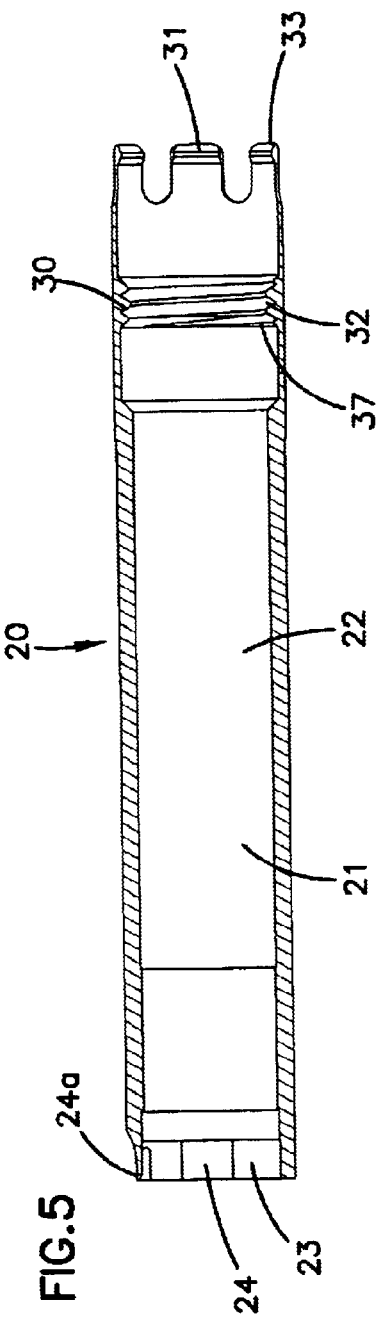
FIG. 5 is a longitudinal cross section view of the outer cannula of the temporary fixation device of FIG. 1.

Referring to FIGS. 2 and 5 (FIG. 5 is a longitudinal cross section view through outer cannula 20), it will be appreciated that the interior surface 22 at the distal end of outer cannula 20 includes a coaptating region 23 having a hexagonal configuration 24 for coaptating with the external hexagonal configuration 120 of locking nut 111. Tab 24a provides an inwardly directed force to hold locking nut 111 in place within coaptating region 23.

As best seen in FIG. 2, the exterior surface 25 of outer cannula 20 also includes a driver engagement region 26 having a hexagonal configuration 27 for engaging cannula engagement region 81 at the distal end of lumen 82 of driver 80. As discussed earlier, the driver engagement region 26 of TFD 10 can have a splined configuration 27a complimentary to cannula engagement region 81a of driver 80 as shown in FIGS. 3a–3c.

Thus, when cannula engagement region 81 of driver 80 is positioned over driver engagement region 26 of cannula 20 and the coaptating region 23 of cannula 20 is positioned around locking nut 111, rotation of driver 80 causes rotation of locking nut 111 to threadedly apply locking nut 111 onto threads 109 and 110. FIGS. 1, 3a, 3b and 4 illustrate that outer cannula 20 can substantially cover the external hexagonal configuration 120 of locking nut 111 when coaptating region 23 is mounted to locking nut 111. The proximal end of driver 80 can include a handle receiving region 84 for mounting a handle (not shown) to facilitate rotation of driver 80. Suitable handles for rotating driver 80, including torque limiting handles, are known and can be used.

Figure 6:
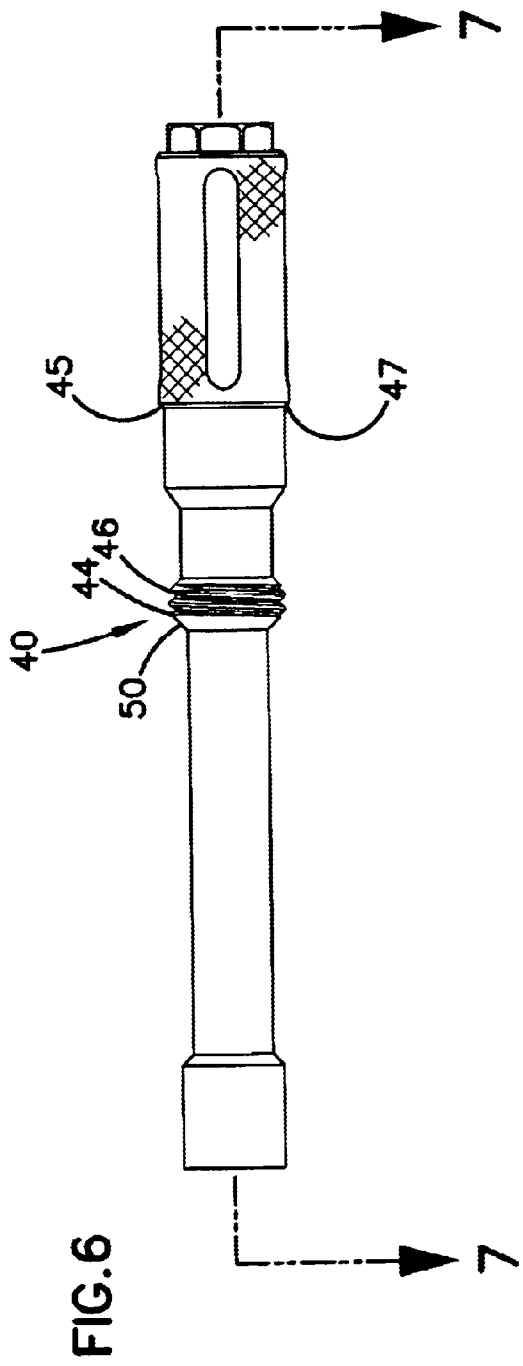
FIG. 6 is a side view of an inner cannula of a temporary fixation device according to the invention.
Figure 7:
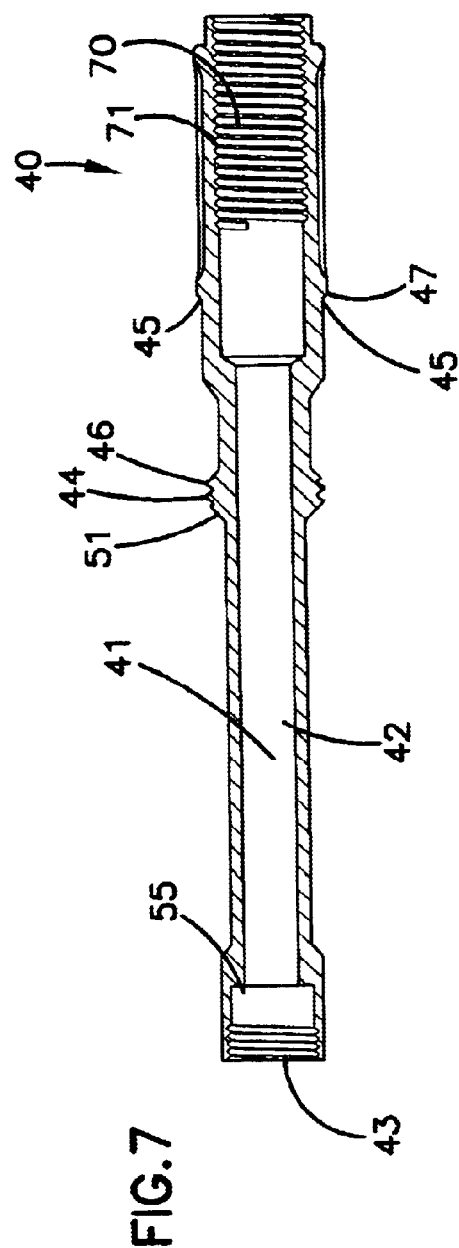
FIG. 7 is a longitudinal cross section view through lines 7—7 of the inner cannula of FIG. 6.

FIG. 6 is a side view of one embodiment of an inner cannula 40 according to the invention and FIG. 7 is a longitudinal cross section of the inner cannula 40 of FIG. 6 taken through line 7—7. As illustrated, the interior surface 42 of lumen 41 of inner cannula 40 can include threads 43 at the distal end. In this embodiment, threads 43 are sized to threadedly mate with proximal threads 110 of spinal implant 101.

Referring to FIGS. 4–7, when inner cannula 40 is positioned within lumen 21 of outer cannula 20, outer cannula 20 is axially movable over inner cannula 40 between a distally advanced and proximally retracted position. In the illustrated embodiment, the limits of the proximally retracted and distally advanced positions, of outer cannula 20 are determined by the interaction of inner cannula distal stop 44 and inner cannula proximal stop 45 with outer cannula distal stop 30 and outer cannula proximal stop 31. In the illustrated embodiment, inner cannula distal stop 44 comprises an external helical thread 46 and inner cannula proximal stop 45 comprises ridge 47. Outer cannula distal stop 30 comprises an internal helical thread 32 which can threadedly mate with external helical thread 46 of inner cannula 40. The outer cannula proximal stop 31 comprises one or more fingers 33 positioned to abut against ridge 47 of inner cannula 40.

Axial mobility of outer cannula 20 over inner cannula 40 may be best understood by referring to FIGS. 4, 5 and 6. Initially, inner cannula 40 is passed into outer cannula 20 and axially rotated such that external helical threads 46 of inner cannula distal stop 44 threadedly engage internal helical threads 32 until external helical threads 46 of internal cannula 40 pass distally beyond and disengage from internal helical threads 32 of outer cannula 20. Once external helical threads 46 are advanced distally beyond internal threads 32 (see FIG. 4) outer cannula 20 can be slid proximally until fingers 33 of outer cannula proximal stop 31 abuts against ridge 47 of inner cannula proximal stop 45. From the proximally retracted position, outer cannula 20 can be distally advanced until the proximal aspect 37 of internal helical threads 32 of outer cannula 20 abut against the distal aspect 50 of external helical threads 46 of inner cannula 40. The relative position of the fingers 33 of outer cannula proximal stop 31 and ridge 47 of inner cannula proximal stop 45 can be seen with outer cannula 20 in the distally advanced position in FIG. 1 and in the proximally retracted position in FIG. 3b.

As shown in FIG. 7, the interior surface 42 of lumen 41 of inner cannula 40 also includes an axially directed shoulder 55. Shoulder 55 can affirmatively stop distal advancement of inner cannula 40 against the proximal edge 122 of implant 101 when threads 43 of inner cannula 40 are threadedly advanced along thread set 110 of implant 101.

Figure 8:
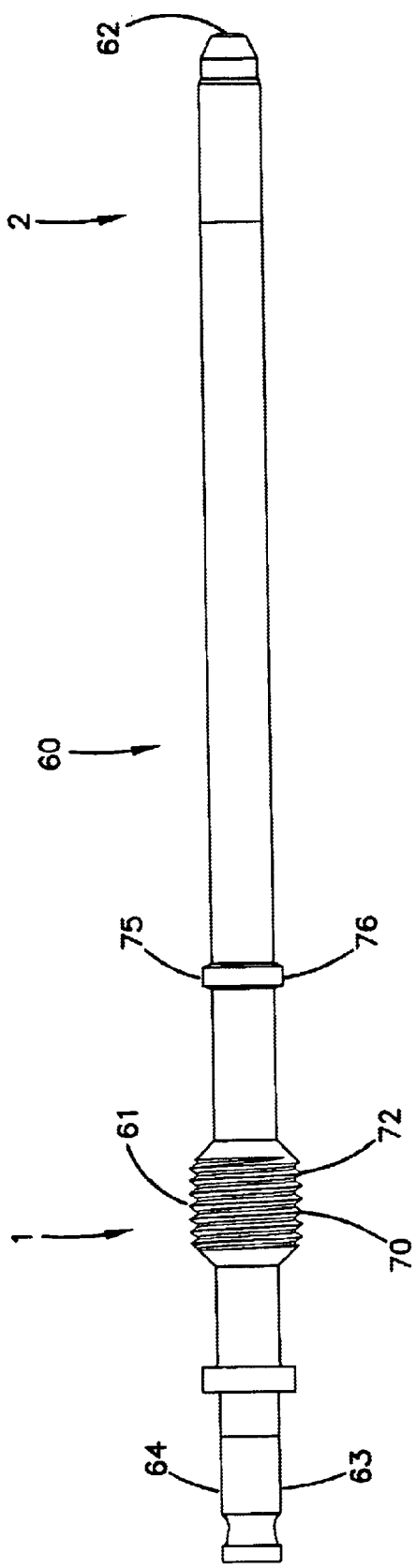
FIG. 8 is a side view of one embodiment of a fixing member according to the invention.
Figure 9:
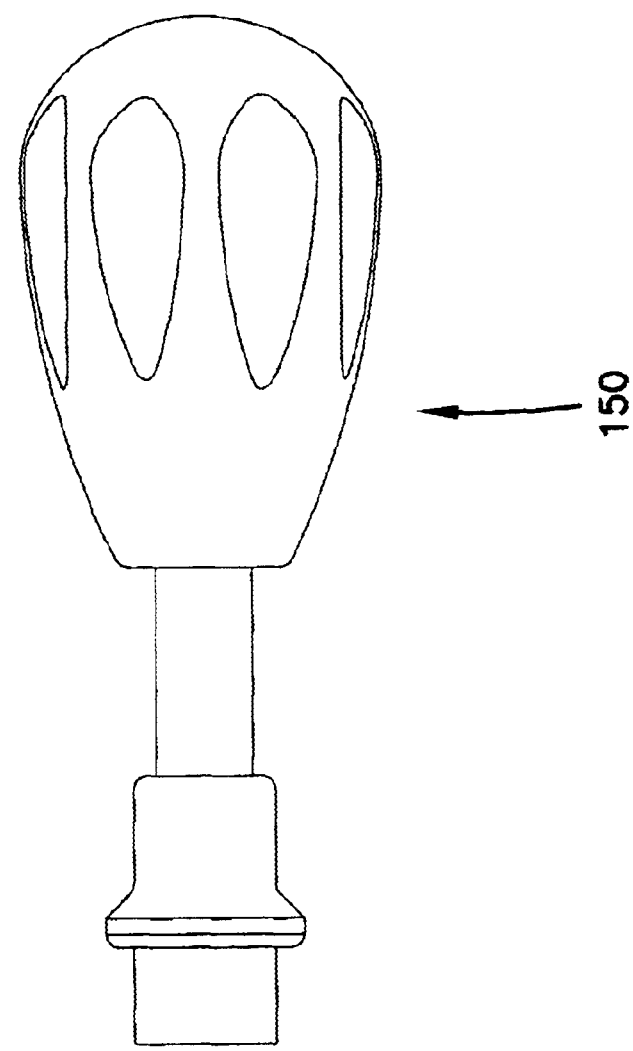
FIG. 9 is a side view of an embodiment of a handle suitable for use according to the invention.

Referring to FIG. 8, fixing member 60 includes a distal tip 62 and an operating end 63 including a handle receiving portion 64 configured for receiving a handle such as handle 150 shown in FIG. 9. A centering guide 75 such as annular collar 76 can be provided to maintain fixing member 60 centered within lumen 41 of inner cannula 40. Referring to FIGS. 4 and 7, fixing member 60 also includes a portion of a temporary securing arrangement 70 to temporarily secure the fixing member in a position to temporarily fix rod 102. In the illustrated embodiment, temporary securing arrangement 70 includes threads 61 on fixing member 60 which threadedly engage proximal internal threads 71 on inner cannula 40. Threadedly rotating threads 61 of fixing member 60 relative to proximal internal threads 71 of inner cannula 40 provides for selective axial advancement and retraction of fixing member 60 within inner cannula 40 to secure fixing member 60 against the surface of rod 102 for temporary fixation of rod 102 in cradle region 106 of spinal implant 101. While the illustrated embodiment utilizes threads for advancing, retracting and securing fixing member 60, alternative temporary securing arrangements can be used including, for example, a locking cam, pneumatic pressure, etc.

According to one method of the invention, a spinal implant 101 can be anchored to the vertebral body using known procedures (e.g., threads, hooks, etc.). A rod securing arrangement, such as locking nut 111 can be positioned into the coaptating region 23 of outer cannula 20 of TFD 10. At this stage, driver 80 of TFD 10 may be absent and thus TFD 10 appears substantially as shown in FIGS. 1 and 3b. Locking nut 111 can then be threaded beyond distal threads 109 and just started onto proximal threads 110 of arms 107 and 108 by rotating outer cannula 20. At this stage, the appearance of TFD 10 relative to spinal implant 101 will be substantially as shown in FIG. 3b. As locking nut 111 is advanced distally onto the distal threads 109, inner threads 43 at the distal end of lumen 41 of inner cannula 40 begin to engage proximal threads 110. In FIG. 3a, outer cannula 20 has been removed to visualize the appearance of the relationship between the inner cannula 40 and spinal implant 101 at this stage of the procedure.

Rod 102 can then be positioned in cradle region 106. A handle, such as handle 150 (FIG. 9) can be mounted to handle receiving portion 64 at the proximal end of fixing member 60 and fixing member 60 rotated until fixing member 60 exerts a sufficient force to immobilize rod 102 with the force exerted by fixing member 60 preferably being exerted along an axis concentric with the longitudinal axis A—A of TFD 10 and spinal implant 101. Fixing member 60 can then be alternately loosened and tightened as necessary during correction maneuvers until the vertebral bodies are in desired position for permanent fixation.

In addition to providing temporary fixation, fixing member 60 also ensures that the rod 101 is fully seated within the cradle 106 of the spinal implant 101. It will be appreciated that at this stage of the procedure, although there may be repeated loosening and tightening of fixing member 60 against rod 102, the locking nut 111 that will maintain permanent fixation of rod 102 within spinal implant 101 post-operatively, has not yet been passed over the distal threads 109, leaving these threads and threads 113 of locking nut 111 in a pristine condition until finally used for permanent fixation. Thus, in one embodiment, in contrast to permanent fixation, TFD 10 provides for temporary fixation of rod 102 within cradle region 106 to permit the surgeon to secure and unsecure rod 102 within cradle region 106 without forcing arms 107 and 108 together against rod 102 with locking nut 111 until a final position of rod 102 is determined for permanent fixation.

Once the optimal position of the vertebral bodies is determined, handle 150 can be removed from fixing member 60. Driver 80 can then be passed onto TFD 10 such that cannula engaging region 81 of driver 80 engages the corresponding exterior surface contour 26 of outer cannula 20. The outer cannula 20 can then be rotated by driver 80 to advance locking nut 111 distally along distal threads 109 to secure surface 112 of locking nut 111 against rod 102. A handle such as handle 150 (FIG. 9) or a "T" handle or other known handle can be used to rotate driver 80. In one preferred embodiment a torque limiting wrench can be used to finally tighten all locking nuts on all implants used. The appearance of the spinal assembly 100 and TFD 10 at the final stage of the procedure is substantially as shown in FIG. 1. Note that at this stage, axially extending fingers 33 at the proximal end of outer cannula 20 are distally advanced away from ridge 47 of outer cannula 20.

To remove the TFD 10, fixing member 60 is threadedly retracted away from rod 102. The outer cannula 20 can then be proximally retracted such that the coaptating region 23 at the distal end of outer cannula 20 is free from locking nut 111. Inner cannula 40 can then unthreaded from the proximal thread set 110 of spinal implant 101. If present, tabs 118 and 119 of arms 107 and 108 can be broken free from the spinal implant at grooves 116 and 117, respectively. The surgical incision can then be closed using known methods.

Figure 10:
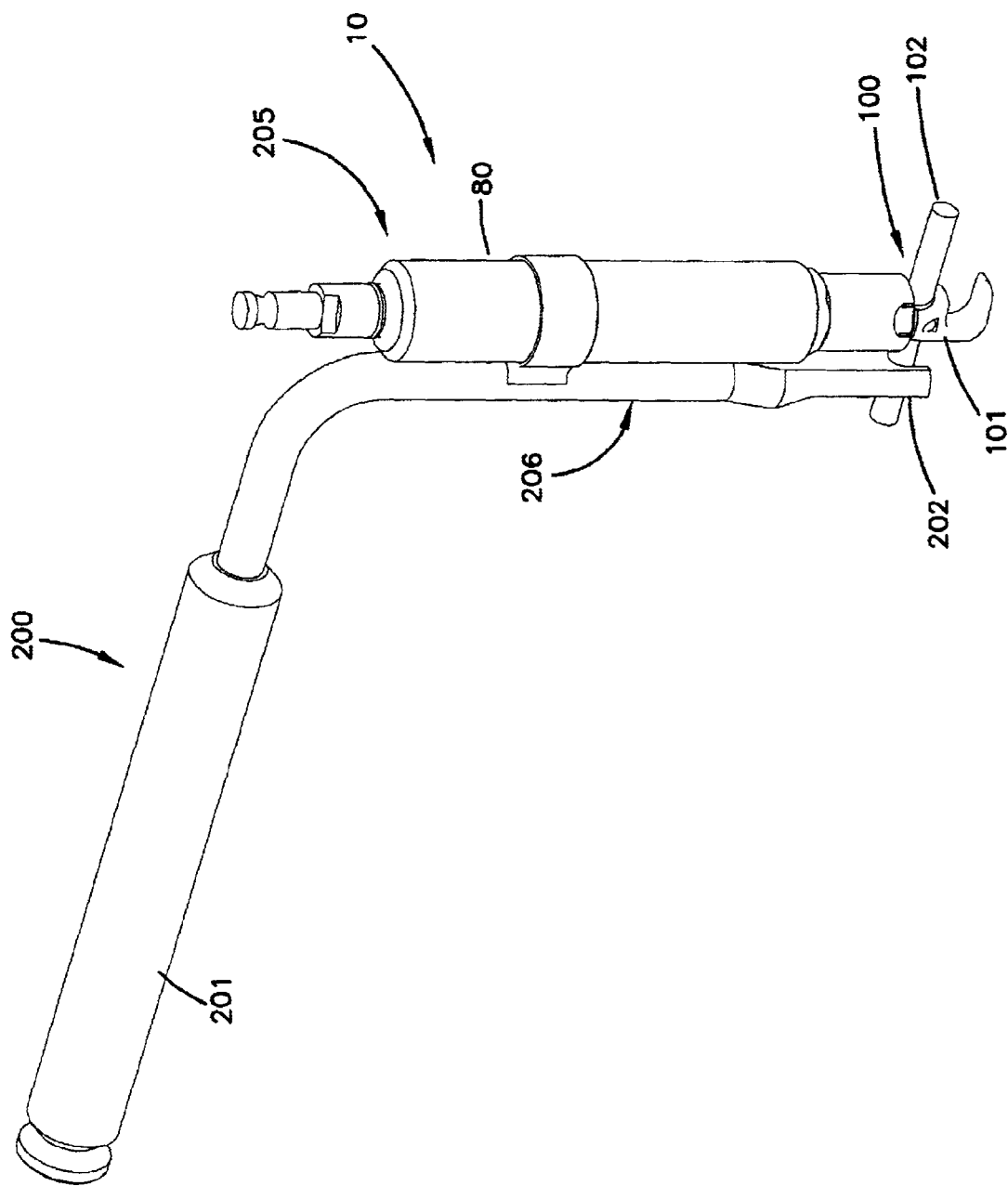
FIG. 10 illustrates one embodiment of an anti-torque arrangement according to the invention.

FIG. 10 illustrates one embodiment of an anti-torque arrangement 200 suitable for use with a TFD 10 according to the invention. As illustrated, anti-torque arrangement 200 can include a handle 201 for gripping and a rod stabilizing arrangement 202 for grasping a portion of rod 102. Thus, when driver 80 is rotated in the direction of arrow 205 to tighten a locking nut, such as locking nut 111, handle 150 can be used to provide an anti-torque force in the direction of arrow 206 to counteract the forces on the assembly 100 during final tightening of the locking nuts.

Figure 11:
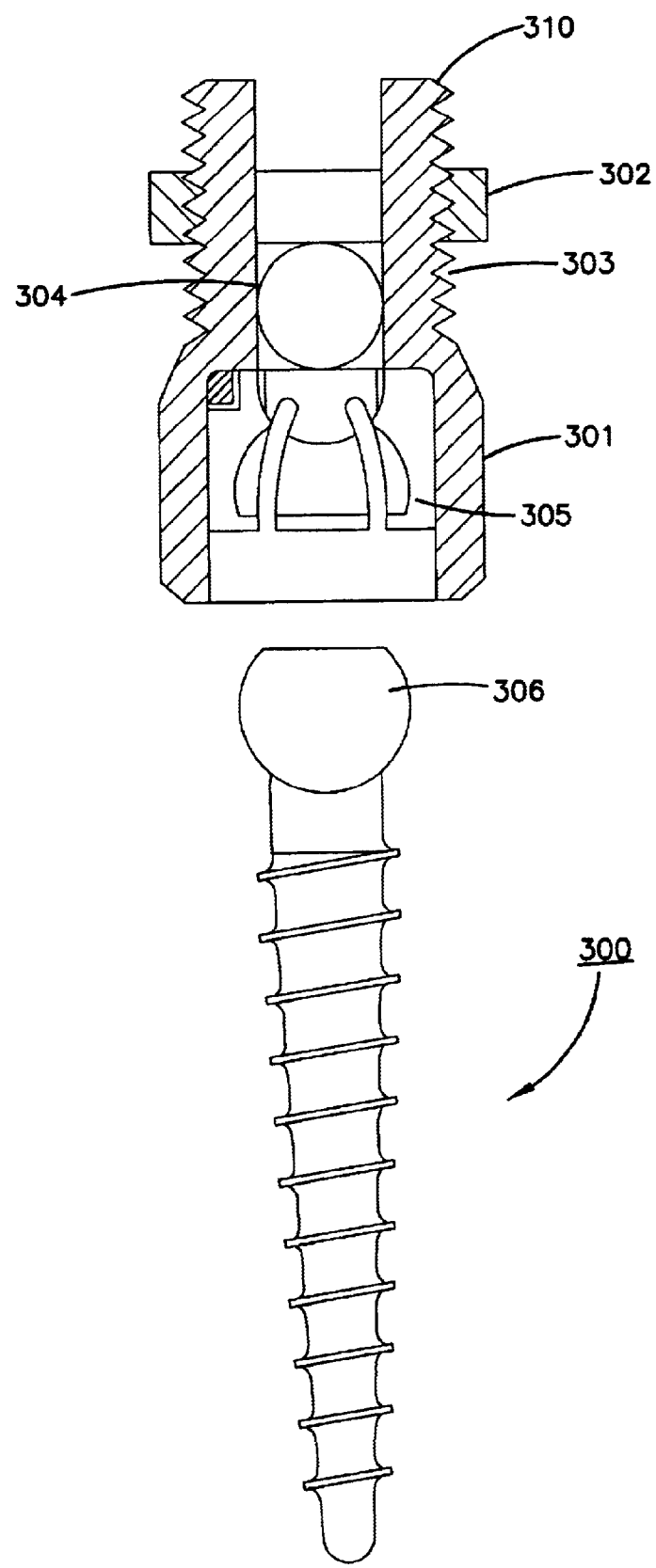
FIG. 11 illustrates a pedicle screw with a polyaxial head that can be set according to one embodiment of the invention.

In another embodiment, a TFD 10 can be advantageously used to "set" or cold fuse the polyaxial head of a pedicle screw having a polyaxial head, such as disclosed in U.S. Pat. Nos. 5,964,760 and 6,010,503. FIG. 11 illustrates one embodiment of a pedicle screw 300 having a polyaxial head 301. Typically, the mobility of polyaxial head 301 is set when locking nut 302 is advanced distally along distal threads 303 to force rod 304 against insert 305 which tightens around screw head 306 to set polyaxial head 301 in a fixed position. Once the position of polyaxial head 301 is fixed, locking nut 302 can be loosened, if it is necessary to reposition rod 304, without concern that the position of polyaxial head 301 will change. However, rather than tightening and loosening locking nut 302 to fix polyaxial head 301, a TFD 10 can be used to set polyaxial head 301 to maintain distal thread set 303 in a pristine condition until permanent fixation.

According to this embodiment, internal threads 43 of inner cannula 40 are threaded onto proximal threads 310 of pedicle screw 300. Fixing member 60 can then be distally advanced to exert a force against rod 304 and insert 305 to set polyaxial head 301 in a fixed position on screw head 306. Corrective maneuvers can then be performed with TFD 10 as described above without movement of the position of polyaxial head 301 and without the need to advance locking nut 302 along distal threads 303, until a permanent fixation position is determined.

From the foregoing detailed description it will be evident that modifications and variations can be made in the devices and methods of the invention without departing from the spirit or scope of the invention. Therefore, it is intended that all modifications and variations not departing from the spirit of the invention come within the scope of the claims and their equivalents.

We claim:

1. A method for stabilizing the spinal column comprising:
    anchoring a first bone implant to a first vertebral body, the first bone implant having a first rod receiving arrangement;
    positioning a stabilizing rod in the first rod receiving arrangement of the first bone implant;
    applying a first rod securing device to the first bone implant;
    mounting a temporary fixation apparatus to the first bone implant, the temporary fixation apparatus including a fixing member;
    fixing the stabilizing rod in position by passing the fixing member of the temporary fixation apparatus through a portion of the first bone implant to secure the stabilizing rod in position;
    fixing the stabilizing rod in position with the first rod securing device.

2. The method according to claim 1 further comprising anchoring a second bone implant to a second vertebral body, the second bone implant having a second rod receiving arrangement.

3. The method according to claim 2 comprising positioning the stabilizing rod in the second rod receiving arrangement of the second bone implant.

4. The method according to claim 1 wherein the rod receiving arrangement of the first bone implant comprises a cradle including a plurality of arms and the fixing member is passed between the arms to rest in the cradle.

5. The method according to claim 1 further comprising a step of removing the temporary fixation apparatus from the fist bone implant.

6. The method according to claim 1 wherein the first rod securing device is a locking nut.

7. The method according to claim 1 wherein the first bone implant includes a cradle having a plurality of arms having threads on an exterior surface of the arms for threadedly mounting the first rod securing device.

8. The method according to claim 1 wherein the temporary fixation apparatus comprises:
    an outer cannula having a proximal end, distal end and a first lumen passing therebetween; and
    an inner cannula having a proximal end, distal end and second lumen passing therebetween; and
    the fixing member passed through the second lumen.

9. The method according to claim 1 wherein the first bone implant is a pedicle screw.

10. The method according to claim 1 wherein the first bone implant includes a hook for mounting to the first vertebral body.

11. The method according to claim 1 wherein the first bone implant has a longitudinal axis and the temporary fixation apparatus has a longitudinal axis such that the fixing member fixes the stabilizing rod in position along an axis coaxial with the longitudinal axis of the spinal implant.

12. The method according to claim 1 further comprising a step of:
   unsecuring the stabilizing rod;
   altering the position of a vertebra of the spinal column; and
   resecuring the stabilizing rod.

13. A method for stabilizing the spinal column comprising:
   anchoring a first bone implant to a first vertebral body, the first bone implant having a first rod receiving arrangement;
   positioning a stabilizing rod in the first rod receiving arrangement of the first bone implant;
   applying a rod securing device to the first bone implant;
   mounting a temporary fixation apparatus to the first bone implant, the temporary fixation apparatus comprising a cannula and a fixing member positioned within the cannula;
   temporarily fixing the stabilizing rod in position by passing the fixing member through the cannula and a portion of the first bone implant to fix the stabilizing rod in position;
   securing the stabilizing rod in position with the rod securing device.

14. The method of claim 13 wherein temporarily fixing the stabilizing rod in position comprises adjusting the position of the stabilizing rod within the implant by tightening or loosening the fixing member against the stabilizing rod while maintaining a position of the cannula mounted to the implant.

* * * * *